United States Patent [19]

Devon et al.

[11] Patent Number: 4,851,581
[45] Date of Patent: Jul. 25, 1989

[54] CHELATE LIGANDS FOR LOW PRESSURE HYDROFORMYLATION CATALYST AND PROCESS EMPLOYING SAME

[75] Inventors: Thomas J. Devon; Gerald W. Phillips; Thomas A. Puckette; Jerome L. Stavinoha; Jeffrey J. Vanderbilt, all of Longview, Tex.

[73] Assignee: Eastman Kodak Company, Rochester, N.Y.

[21] Appl. No.: 60,693

[22] Filed: Jun. 11, 1987

Related U.S. Application Data

[62] Division of Ser. No. 873,918, Jun. 13, 1986, Pat. No. 4,694,109.

[51] Int. Cl.[4] ............................................. C07F 9/02
[52] U.S. Cl. ........................................ 568/17; 556/70;
568/454; 502/166
[58] Field of Search ............... 568/454, 17; 502/166;
556/70

[56] References Cited

U.S. PATENT DOCUMENTS 4,694,109  9/1987  Devon et al. .................. 568/454

FOREIGN PATENT DOCUMENTS 55-61937  5/1980  Japan ................................. 502/166
7016532  5/1971  Netherlands ...................... 502/166
2056874  3/1981  United Kingdom ............. 502/166

OTHER PUBLICATIONS

Huheey, *Inorganic Chemistry*, Harper & Row, NY, (1978), p. 721.
Chemical Abstracts, 87(15):117707y; 91(11):91764v; 104(14):110261j.

*Primary Examiner*—William R. Dixon, Jr.
*Assistant Examiner*—Andrew Griffis

*Attorney, Agent, or Firm*—S. E. Reiter; William P. Heath, Jr.; J. Ferderick Thomsen

[57] ABSTRACT

A novel ligand for use in hydroformylation reactions wherein at least one olefin having from 2 to 20 carbon atoms is contacted in a reaction zone at a temperature of from about 20° C. to about 250° C. and a pressure of from about 50 psig to about 800 psig with hydrogen, carbon monoxide, and a catalyst containing rhodium, the ligand having the formula

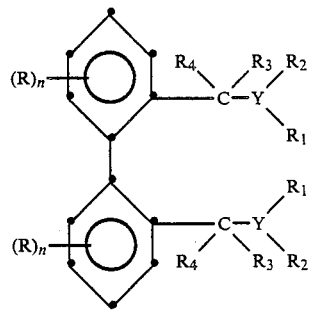

wherein:
  n is 1-4;
  each R is independently selected from hydrogen, alkyl, alkoxy, aryloxy, aryl, aralky, alkaryl, alkoxyalkyl, cycloaliphatic, halogen, alkanoyl, alkanoyloxy, alkoxycarbonyl, carboxyl or cyano;
  each $R_1$ and $R_2$ is independently selected from alkyl, aryl, aralkyl, alkaryl or cycloaliphatic;
  each $R_3$ and $R_4$ is independently selected from hydrogen and the $R_1$ substituents; and
  each Y is independently selected from the elements N, P, As, Sb and Bi.

4 Claims, No Drawings

CHELATE LIGANDS FOR LOW PRESSURE HYDROFORMYLATION CATALYST AND PROCESS EMPLOYING SAME

This is a divisional of application Ser. No. 873,918 filed on June 13, 1986 and now U.S. Pat. No. 4,694,109.

This invention concerns novel chelate ligands and hydroformylation catalysts and processes employing the same wherein one or more olefins and/or other unsaturated organic compounds may be converted to aldehydes for use as such or for conversion by known methods, to produce such as alcohols and acids. More particularly, the invention concerns ligands especially useful for oxo or hydroformylation processes designed for relatively low pressure operation for the preparation of unusually high proportions of normal or unbranched aldehydes from α-olefins, particularly n-butyraldehyde from propylene.

The present ligands are compounds of the formula

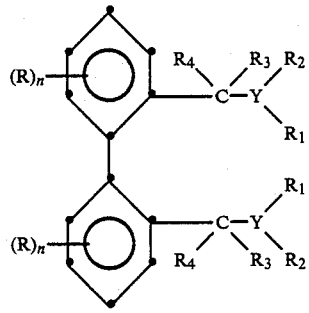

useful as ligands in hydroformylation and other reactions, wherein:

n is 1-4;

each R is independently selected from hydrogen, alkyl, alkoxy, aryloxy, aryl, aralkyl, alkaryl, alkoxyalkyl, cycloaliphatic, halogen, alkanoyl, alkanoyloxy, alkoxycarbonyl, carboxyl or cyano;

each $R_1$ and $R_2$ is independently selected from alkyl, aryl, aralkyl, alkaryl or cycloaliphatic;

each $R_3$ and $R_4$ is independently selected from hydrogen and the $R_1$ substituents;

each of the above alkyl groups or moieties is straight or branched chain of 1-20 carbons, each aryl group contains 6-10 ring carbons, and each cycloaliphatic group contains from 4-6 ring carbons; and each Y is independently selected from the elements N, P, As, Sb and Bi, with P being preferred.

The present hydroformulation process in its broad sense comprises contacting at least one olefin having from 2 to 20 carbon atoms in a reaction zone at a temperature of from about 20° C. to about 250° C. and a pressure of from about 50 psig to about 800 psig with syn gas ($H_2$, CO) and a catalyst comprising rhodium in chemical complex with one or more of the above ligands for a sufficient period of time to permit reaction of said olefin with said syn gas to form aldehyde product.

The present preferred 2,2'-bis(phosphinomethyl)-1,1'-biphenyl ligand class has great utility as a bidentate ligand modifier for the low pressure rhodium hydroformylation of alpha-olefins to prepare aldehyde products with unusually high ratios of normal to branched isomers. This invention effects the efficient use of olefinic feedstocks to prepare desirable linear aldehyde products in high yield. Such products from propylene include n-butyraldehyde which is used to prepare the commercial solvent n-butanol. The hydroformylation of 1-butene and 1-pentene yield intermediate aldehyde products useful for the preparation of the solvents 1-pentanol and 1-hexanol, respectively. The hydroformylations of 1-hexene and 1-octene yield aldehyde products used to prepare the commercially valuable carboxylic acids, n-heptanoic acid and n-nonanoic acid. These same aldehyde products may be converted into alcohols useful for the preparation of plasticizers, synthetic lubricants, and detergents. Likewise, the hydroformylation of higher olefins such as 1-decene and 1-dodecene yield aldehyde precursors to 1-undecanol and 1-hydroxytridecane useful as fabric softeners and ingredients in plasticizers and detergents. These ligands show improvements in hydroformylation technology in one or more areas such as high normal to iso ratios employing relatively small amounts of ligand, effective in low pressure systems, increased catalytic activity and retention thereof over extended periods, and increased catalyst stability. The ligands of the invention are particularly useful in their unique ability to produce the desired high normal/iso ratios even at desirable low levels of ligand.

Preferred of the present ligands are: 2,2'-bis(diphenylphosphinomethyl)-1,1'-biphenyl; 2,2'-bis(dibenzylphosphinomethyl)-1,1'-biphenyl; 2,2'-bis(phenylbenzylphosphinomethyl)-1,1'-biphenyl; and 2,2'-bis(diisobutylphosphinomethyl)-1,1'-biphenyl. As a general statement of the actual chemical composition of the present active catalyst species in the reaction zone, the species preferably comprises rhodium complexed with (a) a ligand defined by the above structural formula in a molar ratio of ligand/Rh of about 1/1, (b) H in a molar ratio of H/Rh of about 1/1, and (c) carbon monoxide in a molar ratio of CO/RH of about 2/1.

The present process is carried out preferably in a gas sparged reacted such that the catalyst does not leave the reaction zone with the aldehyde product which is taken overhead by the unreacted gases. The overhead gases are then chilled in a vapor liquid separator to condense out the aldehyde product, the gases being recycled to the reactor and the liquid product let down to atmospheric pressure for separation and purification by conventional techniques. A side draw from the reactor preferably is provided so that a small amount of the catalyst can be withdrawn at a desirable rate for more complete distillation and/or regeneration and returned to the reactor after the addition of make-up ligand thereto.

The metal catalyst components are charged preferably with solvent to the reactor through suitable pressurized pumping means, preferably in their soluble forms, e.g., their carboxylate salts or mineral acid salts or the like well known to the art as disclosed, for example, in U.S. Pat. No. 2,880,241. Charged therewith or separated is one or more of the present modifying ligands in amount such that the molar ratio of ligand to rhodium in the reactor is from about 1.0 to about 200 or more, preferably from about 2.0 to about 10.0, and most preferably from about 2.3 to about 4.0.

The process is particularly effective at pressures from about 50 to about 800 psig with from about 100 to about 400 psig being preferred, and from about 240 to about 280 psig being most preferred. The reaction temperatures can vary from about 20° to about 250° C., but preferably from about 50° to about 175° C. and most preferably from about 80° to about 150° C. In a highly preferred embodiment, the above process is carried out wherein at steady state hydroformylation conditions in said reaction zone the ratio of Rh(mg.)/solvent (ml) is from about 0.07 to about 0.28, the ratio of [olefin feed in liters (STP)/min]/mg. of Rh is from about 0.03 to about 0.09, the ratio of [CO or $H_2$ feed in liters (STP)/min]/mg. of Rh is from about 0.015 to about 1.5, the temperature is maintained at from about 80° C. to about 150° C., and the reactor pressure is maintained at from about 240 psig to about 280 psig. The term "STP" refers to standard temperature of 273° K. and standard pressure of 760 mm Hg.

In the process, the syn gas is introduced into the reactor in a continuous manner by means, for example, of a primary compressor, and the ratio of hydrogen to carbon monoxide in the feed may be selected according to the particular olefin being hydroformylated and the reaction conditions present, as is well known in the art. Generally, the molar ratio of hydrogen to carbon monoxide in the reactor is maintained within the range of about 0.5 to about 4.0, but it has been found in many hydroformylations that the rate of reaction as well as yield of the desired product may be increased by increasing the hydrogen to carbon monoxide molar ratio above 4.0, and up to about 10.0 or more. The syn gas preferably is present in a molar excess (total moles of $H_2+CO$) with respect to the olefin and the molar ratio varies typically from about 0.5 to about 20, preferably from about 1.2 to about 6. In a liquid overflow reactor, the above molar ratio may have a lower limit of about 0.02.

The olefin is fed to the reactor by means of suitable pumps capable of operating under substantial pressures, and the feed rates of the olefin and syn gas are selected to maintain the above-recited molar ratios of these reactants in the reactor. Typical olefins to which the present invention is applicable include straight or branched chain α-olefins containing from 2 to 20 carbon atoms and preferably from 2 to 10 carbon atoms, and optionally containing groups or substituents which do not interfere with the hydroformylation process. Illustrative of such α-olefins are ethylene, propylene, 1-butene, 2-methylpropylene, 2-methyl-1-butene, 1-pentene, 1-hexene, 1-heptene, 1-octene, 2-ethyl-1-hexene, 1-dodecene and 1-octadecene. Also useful with the present invention are the internal olefins such as butene-2 and cyclic olefins such as cyclooctene. If desired, mixtures of olefins, particularly ethylene and propylene, can be fed to the reactor.

Any suitable solvent which does not adversely affect the hydroformylation process and which is inert with respect to the catalyst, olefin feed, syn gas and the hydroformylation products may be used. Inert solvents of this nature are well known to those skilled in the art and include benzene, xylene, toluene and their substituted derivatives, pentanes, naphtha, kerosene, mineral oils, cyclohexane, cyclopentane, ethers, esters, etheresters, alcohols, acetals, ketones, and various mixtures thereof. Preferred solvents are those which are sufficiently high boiling to remain for the most part in the gas sparged reactor, and include 2,2,4-trimethyl-1,3-pentanediol monoisobutyrate (TMPDMI), and its isomers, and the by-products such as alcohols, esters, acetals, and hydroxyaldehydes produced in the hydroformylation reaction and retained as high boiling liquids at the bottom of the subsequent distillation columns.

The present process can be carried out with very small amounts of catalyst containing from about $1 \times 10^{-6}$ moles of rhodium (calculated as Rh°) per mole of olefin in the reactor zone. However, such low catalyst concentrations are not commercially desirable since the reaction rates are low. The upper catalyst concentration is essentially unlimited and appears to be dictated principally by the high cost of rhodium and the fact that no advantage is evident in the use of catalyst containing above about $1 \times 10^{-1}$ moles of rhodium per mole of olefin in the reactor zone. A concentration of from about $1 \times 10^{-5}$ moles to about $5 \times 10^{-2}$ moles of rhodium per mole of olefin is preferred, and from about $1 \times 10^{-4}$ to about $1 \times 10^{-2}$ is mpost preferred.

This invention will be illustrated further by the following examples although it will be understood that these examples do not limit the invention and are for purposes of illustration only. The synthesis of the present chelating diphosphine ligands is straightforward thus making them easily prepared in practical quantities. Below are given some of the synthetic routes available to prepare the ligands, the phosphorylation of 2,2'-bis(bromomethyl)-1,1'-biphenyl by alkali metal "M" phosphine anions being a particularly useful synthesis. Examples are given herein of the synthesis of the bis(diphenylphosphino), bis(phenylbenzylphosphino), and bis(diisobutylphosphino) derivatives using this method (Reaction I). Likewise, the diphosphino chelate ligands may be prepared by the oxyphosphorylation of the above dibromo compound by its reaction with alkali metal salts of the phosphine oxide anion and subsequent reduction to the diphosphine chelating ligand (Reaction II) by any of a number of reducing agents such as lithium aluminum hydride.

Reaction I

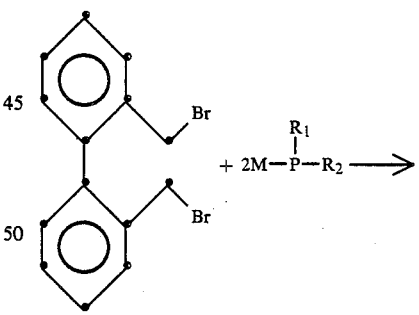

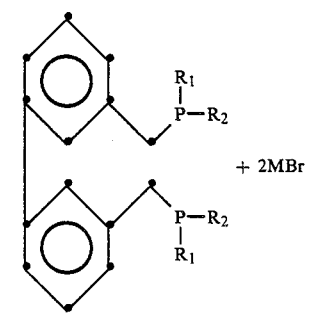

Reaction II

-continued

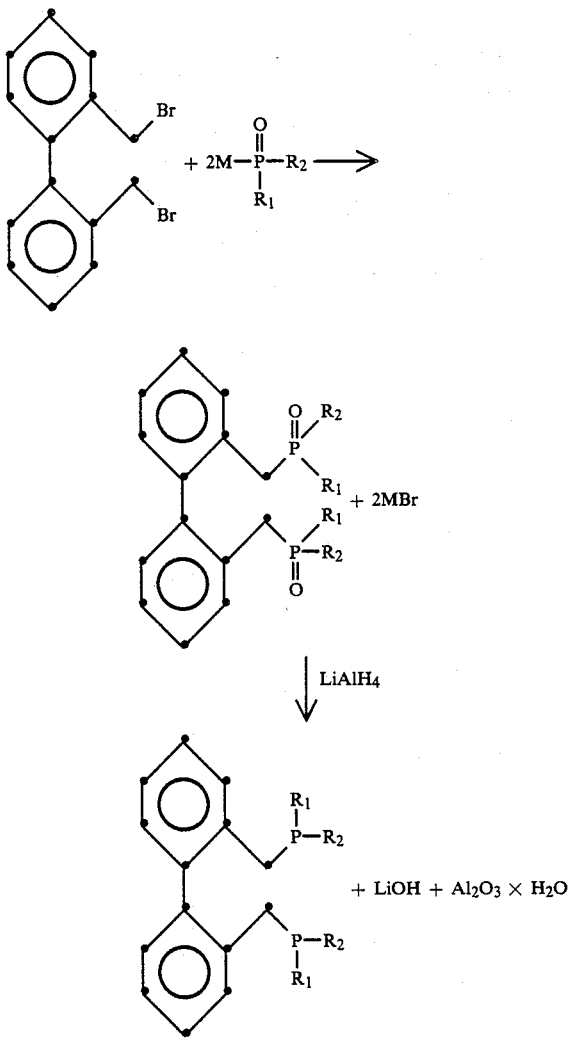

The above 2,2'-bis(bromomethyl)-1,1'-biphenyl intermediate is prepared in high yield from 2,2'-bis(hydroxymethyl)-1,1'-biphenyl by its reaction with PBr₃. The diol precursor is easily obtained in known manner by either standard catalytic hydrogenation or by lithium aluminum hydride reduction of diphenic acid. The diol is also easily prepared by reduction of 2,2'-bis(formyl)-1,1-biphenyl, obtained by the high yield ozonolysis of phenanthrene in known manner.

All experimental procedures involving phosphines or organometallic compounds were run under an atmosphere of nitrogen using dry, deoxygenated solvents. Tetrahydrofuran (THF) was distilled under nitrogen from sodium/benzophenone ketyl. Chemical shifts for nuclear magnetic resonance (NMR) spectra are reported in parts per million ($\delta$) downfield from tetramethylsilane for $^1$H NMR spectra and relative to aqueous H₃PO₄ for $^{31}$P NMR spectra.

EXAMPLE 1

2,2'-Bis(hydroxymethyl)-1,1'-biphenyl

Lithium aluminum hydride (12.60 grams, 0.332 mol) and THF (175 ml) were placed in a dry 500 ml three-necked round-bottomed flask fitted with a condenser, addition funnel, nitrogen inlet, and magnetic stirrer. The mixture was cooled with an ice bath and diphenic acid (40.00 grams, 0.165 mol) in THF (100 ml) was added dropwise to the stirring mixture. After the addition was complete, the flask was removed from the ice bath and allowed to warm to room temperature. The reaction mixture was heated at reflux for 2 hours, then stirred overnight at room temperature. After cooling the mixture with an ice bath, water (12.6 ml) was added dropwise, followed by the successive dropwise addition of 15% aqueous sodium hydroxide (12.6 ml) and water (38 ml). The resulting yellow mixture was warmed to room temperature, and the solids were separated by vacuum filtration. The filtrate was placed on a rotary evaporator to remove the solvent. The remaining brownish-yellow solid was recystallized from toluene-hexane to give 28.60 grams (81% yield) of light brown solid product, melting point 105° to 108° C. $^1$H NMR (CDCl₃): $\delta$ 2.77 (br s, 2H, —OH); 3.95 (s, 4H, —CH₂—); 6.50–7.25 (m, 8H, aromatic).

EXAMPLE 2

2,2'-Bis(bromomethyl)-1,1'-biphenyl 2,2'-Bis(hydroxymethyl)-1,1'-biphenyl (25.00 grams, 0.117 mol) and methylene chloride (200 ml) were placed in a 500 ml round-bottomed flask equipped with a magnetic stirrer and an addition funnel with a CaCl₂ drying tube. The stirred mixture was cooled with an ice bath, and phosphorus tribromide (23.1 ml, 66.50 grams, 0.246 mol) was added dropwise from the addition funnel. After the addition was complete, the reaction mixture was removed from the ice bath and stirred overnight at room temperature. The mixture was again cooled with an ice bath, and water (35 ml) was added slowly. After stirring for 1 hour, additional water (75 ml) was added. The layers were separated in a separatory funnel, and the aqueous layer extracted twice with CH₂Cl₂. The combined organic layer was washed with saturated aqueous NaHCO₃ and water and was then dried with MgSO₄. The solvent was removed on a rotary evaporator to give 37.05 grams (93% yield) of light yellow solid which was suitable for use without further purification. The melting point was 85° C. to 88° C. $^1$H NMR (CDCl₃): $\delta$ 4.10 (d, J=10 Hz, 2H, —CH—Br); 4.22 (d, J=10 Hz, 2H, —CH—Br); 6.92–7.53 (m, 8H, aromatic)

EXAMPLE 3

2,2'-Bis(diphenylphosphinomethyl)-1,1'-biphenyl

Diphenylphosphine (10.0 ml, 10.70 grams, 0.057 mol) was dissolved in dry THF (115 ml) under nitrogen in a 300-ml three-necked round-bottomed flask equipped with a magnetic stirrer, addition funnel, and condenser with a nitrogen inlet. The solution was cooled to about −70° C. with a dry ice/acetone bath and n-butyllithium (35.9 ml of a 1.6M solution in hexane, 0.057 mol) was added dropwise from the addition funnel. The orange solution was stirred 1 hour in the cold bath. A solution of 2,2'-bis(bromomethyl)-1,1'-biphenyl (9.30 grams, 0.027 mol) in THF (50 ml) was added dropwise from the addition funnel over about 20 minutes. The solution was allowed to stir overnight at room temperature and was then heated at reflux for 3 hours. Saturated aqueous NH₄Cl (about 50 ml) was added to the stirring solution at room temperature. Diethyl ether (75 ml) was added, and the layers were separated in a separatory funnel. The aqueous layer was extracted twice with diethyl ether. The combined organic solution was washed twice with water. The organic solvent was evaporated on a steam bath under a stream of nitrogen to give a thick, oily residue. The residue was recrystallized from ethanol/diethyl ether to give 10.64 grams (71% yield) of white solid, melting point 84° to 87° C. $^1$H NMR (CDCl$_3$): δ 3.15 (s, 4H, —CH$_2$—); 6.60-7.40 (m, 28H, aromatic). $^{31}$P NMR (CDCl$_3$): δ+9.

EXAMPLE 4

2,2'-Bis(diisobutylphosphinomethyl)-1,1'-biphenyl

Diisobutylphosphine (1.66 grams, 11.37 mmol) was dissolved in THF (25 ml) under nitrogen and cooled with a dry ice/acetone bath. n-Butyllithium (7.11 ml of a 1.6M solution in hexane, 11.37 mmol) was added dropwise to the stirring solution which was then allowed to stir for 1 hour in the cold bath. 2,2'-Bis(bromomethyl)-1,1'-biphenyl (1.89 grams, 5.55 mmol) in THF (10 ml) was added dropwise at −70° C. The solution was allowed to stir overnight at room temperature and was then heated at reflux for 1 hour. Saturated aqueous NH$_4$Cl was added to the solution at room temperature. Diethyl ether was added and the layers were separated in a separatory funnel. The aqueous layer was extracted twice with diethyl ether, and the combined organic solution was then washed twice with water. The solvent was removed on a steam bath under a stream of nitrogen. The oily residue was then placed on a Kugelrohr distillation apparatus to remove low boiling material at about 175° C. and 1 mm Hg leaving 1.88 grams (72% yield) of a thick orange glassy product. $^1$H NMR (CDCl$_3$): δ 0.65-1.67 (complex, 36H, aliphatic); 2.42 (s, 4H, benzylic); 6.67-7.30 (complex, 8H aromatic). $^{31}$P NMR (CDCl$_3$): δ+31.

EXAMPLE 5

2,2'-Bis(dibenzylphosphinomethyl)-1,1'-biphenyl Dioxide

Dibenzylphosphine oxide (6.93 grams, 30.1 mmol) and THF (100 ml) were placed in a 300-ml three-necked flask and cooled at −40° C. under nitrogen. n-Butyllithium (18.84 ml of a 1.6M solution in hexane, 30.1 mmol) was added dropwise from an addition funnel over about 10 minutes and the resulting yellow solution was stirred for 1 hour at −30° C. to −35° C. 2,2'-Bis(bromomethyl)-1,1'-biphenyl (5.00 grams, 14.7 mmol) in THF (20 ml) was added dropwise to the cold solution. When the addition was complete, the solution was warmed to room temperature and was then heated at reflux for 1.5 hours. Saturated aqueous NH$_4$Cl was added and the layers were separated. The aqueous layer was extracted twice with diethyl ether. The combined organic solution was washed with saturated aqueous NaCl. The organic solvent was evaporated on a steam bath under a stream of nitrogen to give a light brown solid. The product was recrystallized from acetone to give a first crop of 3.57 grams (38% yield) of white solid, melting point 203° to 205° C. No attempt was made to recover a second crop. $^1$H NMR (CDCl$_3$): δ 2.07-3.08 (complex, 12H, benzylic); 6.57-7.47 (complex, 28H, aromatic). −P NMR (CDCl$_3$): 67 −43.

EXAMPLE 6

2,2'-Bis(dibenzylphosphinomethyl)-1,1'-biphenyl

Chlorotrimethylsilane (4.1 ml, 32.2 mmol) was added to lithium aluminum hydride (1.22 grams, 32.2 mmol) in THF (20 ml) at −72° C. The mixture was removed from the cold bath, stirred 2 hours, and then cooled again at −35° C. A suspension of the above 2,2'-bis(-dibenzylphosphinomethyl)-1,1'-biphenyl dioxide (3.40 grams, 5.32 mmol) in THF (45 ml) was added by cannula. The mixture was stirred 0.5 hour at −30° C., then overnight at room temperature. The reaction mixture was cooled in an ice bath and quenched by the successive, dropwise addition of water (1.2 ml), 15% aqueous NaOH (1.2 ml) and water (3.6 ml). The resulting mixture was filtered, and the solid was washed with diethyl ether. The filtrate was evaporated on the steam bath under a stream of nitrogen. The residual solid was heated in ethanol, then cooled and filtered to give 2.00 grams (62% yield) of white solid, melting point 163° to 167° C. $^1$H NMR (CDCl$_3$): δ 2.43 (s, 12H, benzylic); 6.50-7.17 (complex, 28H, aromatic). $^{31}$P NMR (CDCl$_3$): δ+9.5.

EXAMPLE 7

2,2'-Bis(benzylphenylphosphinomethyl)-1,1'-biphenyl

Benzyldiphenylphosphine (9.74 grams, 35.3 mmol) was dissolved in THF (100 ml) under nitrogen in a 250 ml three-necked round-bottomed flask equipped with a magnetic stirrer, thermometer, and condenser with a nitrogen inlet. A small amount of naphthalene (0.12 gram) was added followed by the addition of lithium metal (0.49 gram, 70.6 mmol) in small pieces. The mixture quickly became dark reddish-brown and was heated at 40° C. for 6 hours. t-Butyl chloride (2.29 grams, 24.8 mmol) was added dropwise at room temperature, and the mixture was stirred for 0.5 hour. 2,2'-Bis(-bromomethyl)-1,1'-biphenyl (4.71 grams, 13.9 mmol) in THF (20 ml) was added dropwise, whereupon the color changed from dark red-brown to medium orange. The mixture was allowed to stir overnight at room temperature and was then heated at reflux for 1 hour. Water (40 ml) was added and most of the THF was removed on the steam bath under a stream of nitrogen. The aqueous solution was extracted three times with diethyl ether. The combined organic solution was washed with water. The solvent was evaporated to leave an orange oily residue which was placed in a Kugelrohr distillation apparatus and heated at 220° C./1 mm Hg to remove low boiling components, leaving 9.20 grams of an orange glassy solid. $^1$H NMR (benzene-d$_6$): δ 3.28 (br s, 8H benzylic); 6.33-7.33 (complex, 28H, aromatic). $^{31}$P NMR (benzene-d$_6$): δ+10.

EXAMPLE 8

Preparation of Rhodium 2-Ethylhexanoate Solution in Texanol ® Solvent

The apparatus consists of a 5-liter three-necked flask equipped with a heating mantle, Teflon bladed mechanical stirrer, reflux condenser, and a thermometer. Sodium hydroxide (80 grams) was dissolved in 1,000 ml of water in the flask. 2-Ethylhexanoic acid (196 grams) was added to the flask and dissolved. Rhodium chloride hydrate (46.62 grams containing 20 grams of rhodium metal value) was dissolved in 900 ml of water separately and then added to the stirred sodium 2-ethylhexanoate solution in the flask. The mixture was heated to 95° C. and kept vigorously stirred for 1.5 hours. A dark green oil of crude product separated. The mixture was cooled to room temperature and 400 ml of Texanol (2,2,4-trimethylpentane-1,3-diol-monoisobutyrate) solvent was added with stirring. The two phases were separated. The aqueous layer was reextracted with three 400 ml Texanol washes which were combined with the first organic extract. The combined organic phases were washed with 1,000 ml of water. The water wash was combined with the original water wash for rhodium analysis. The combined organic phases were filtered through a 0.5-inch thick bed of celite and made up to 2 liters volume with Texanol that was washed through the celite. The concentration of rhodium in the organic phase was 10,000 ppm and in the combined aqueous phase was 2 ppm.

EXAMPLE 9

Typical Bench-Scale Low Pressure Hydroformylation of Propylene Using Rhodium/2,2'-Bis(diphenylphosphinomethyl)-1,1'-biphenyl Catalyst The reactor consists of a vertically held stainless steel 4 foot by 1 inch (inside diameter) tube having a stainless steel filter element welded into its side near the bottom. The bottom of the tube has a drain valve and the top has a side port through which the vaporized products and unreacted gases leave the reactor. The top end of the tube is provided with a screwed plug which can be removed for charging the catalyst and which contains a thermowell whereby the temperature of the catalyst solution (reaction medium) in the reactor is measured accurately. Hydrogen and carbon monoxide are fed to the reactor from cylinders via pressure regulators and flow controllers which use differential pressure cells and air actuated flow control valves to maintain accurate flow. A third feed of nitrogen from a cylinder goes to the reactor via a pressure regulator and rotameter with needle valve. The carbon monoxide passes through a heated commercial "deoxo" unit as marketed by Engelhard Industries, Division, Engelhard Minerals and Chemicals Corp., Newark, N.J., to remove oxygen impurities. The nitrogen admixed with hydrogen pass through a similar "deoxo" unit before entering the reactor. Propylene is fed as a liquid to a preheater section or plenum chamber, where it is combined with the other feed gases and is vaporized prior to entering the reactor via the stainless steel filter element. The propylene feed rate is measured using rate-of-level drop in a tank containing liquid propylene using an armored rotameter with a needle valve to control the liquid propylene feed rate.

In operation, the catalyst is contained as a solution in the lower portion of the reactor tube and the reactant gases are sparged up through the solution as bubbles emanating from the filter element. Product butyraldehyde is formed in the catalyst solution where it accumulates and eventually is removed as a vapor by vapor/liquid equilibration with unreacted gases. This type of reactor is known as a vapor take-off or vapor stripped reactor. The hot gases are cooled upon leaving the reactor through said side port and the butyraldehyde product, along with some unreacted propylene, collects in a cooled high pressure separator connected by suitable conduit means to said side port. The noncondensed gases are let down to atmospheric pressure via a back pressure regulator which controls the reactor pressure. Additional butyraldehyde is condensed out of the atmospheric pressure gas stream by passing it through a series of three dry ice traps. Once an hour the contents of the high pressure separator and dry ice traps are collected and combined. The weight of butyraldehyde product obtained during the hour and its n/iso ratio are calculated using standard gas/liquid chromatographic techniques in combination with the crude weight of the product collected. In practice, approximately one hour is required for this bench unit to reach steady state production rates where catalyst activity and n/iso product ratio remain substantially constant.

A catalyst charge was prepared as in Example 8 using 2,2'-bis(diphenylphosphinomethyl)-1,1'-biphenyl (0.40 gram, 0.729 mmol) and rhodium 2-ethylhexanoate solution in Texanol containing 31.25 mg (0.304 mmol) of rhodium as the metal in a total volume of 200 ml of Texanol solvent. This preparation was carried out under nitrogen and the catalyst solution charged to the bench unit reactor under argon. After sealing, the reactor was pressured to 260 psig with hydrogen, carbon monoxide, and nitrogen and heated to 125° C. by an external oil bath with said gases purging through the catalyst solution. The gas feed rates at STP were: $H_2=CO=3.36$ liters per minute; and $N_2=0.96$ liter per minute. Propylene feed was then started at 1.92 liters per minute as gas at STP. The run was carried out for a total of 5 hours. Reactor catalyst volume was kept at a standard operating level of 223 ml by pumping in Texanol solvent if level drop occurred as measured by a liquid level differential pressure cell attached to the reactor. The average butyraldehyde production rate for the last 4 hours of operation was 82.3 grams per hour, equivalent to a catalyst activity of 5.80 pounds of butyraldehyde per gram Rh-hour (lb HBu/g Rh-hr) with a very high n/iso ratio of 25.1/1.

EXAMPLE 10

Comparison of Propylene Hydroformylation Runs Using Different Organophosphine Ligands in the Presence of Rhodium Table 1 gives data obtained from several runs in the bench unit hydroformylation reactor wherein different organophosphine ligands were used in the presence of rhodium charged as rhodium 2-ethylhexanoate and operated using the same reactor pressure, catalyst volume, and reactant feed rates as described in Example 9. Table 1 shows the utility of the present ligands, and the exceptional utility of the 2,2'-bis(diphenylphosphinomethyl)-1,1'-biphenyl ligand in producing very high n/iso product ratios in the hydroformylation of propylene.

EXAMPLE 11

Table 2 shows the effect of reaction temperature on the catalyst activity and butyraldehyde n/iso ratio obtained from a 2.4/1 ligand/rhodium mole ratio of the 2,2'-bis(diphenylphosphinomethyl)-1,1'-biphenyl ligand to rhodium. The reactant feed rates, catalyst volume, and reactor pressure are the same as in Example 9. The data show that the n/iso product ratio increases with lower reaction temperature while the catalyst activity decreases.

TABLE 1

| | | Comparison of Different Organophosphine/Rh Catalyst Systems | | | | | |
|---|---|---|---|---|---|---|---|
| Run No. | Ligand | Rh Charge, mg | Ligand Charge, mmol | L/Rh Mole Ratio | Reactor Temp, °C. | Catalyst Activity, lb HBu/g Rh-hr | HBu N/Iso Ratio |
| 1 | BISBI | 31.25 | 0.729 | 2.4/1 | 125 | 5.80 | 25.1/1 |
| 2 | BPBMB | 31.25 | 1.458 | 4.8/1 | 125 | 5.10 | 12.8/1 |

TABLE 1-continued
Comparison of Different Organophosphine/Rh Catalyst Systems

| Run No. | Ligand | Rh Charge, mg | Ligand Charge, mmol | L/Rh Mole Ratio | Reactor Temp, °C. | Catalyst Activity, lb HBu/g Rh-hr | HBu N/Iso Ratio |
|---|---|---|---|---|---|---|---|
| 3 | BDBMB | 31.25 | 0.729 | 2.4/1 | 125 | 0.87 | 3.64/1 |
| 4 | BIBMB | 31.25 | 1.239 | 4.1/1 | 125 | 1.31 | 2.00/1 |
| 5 | TR-DMCB | 31.25 | 0.729 | 2.4/1 | 125 | 5.05 | 4.36/1 |
| 6 | TR-DMECB | 31.25 | 0.729 | 2.4/1 | 125 | 4.41 | 4.23/1 |
| 7 | TR-DPNOR | 31.25 | 0.729 | 2.4/1 | 125 | 4.07 | 4.32/1 |
| 8 | CIS-DPNOR | 31.25 | 0.729 | 2.4/1 | 125 | 2.44 | 2.67/1 |
| 9 | 1,8-DINAP | 31.25 | 0.729 | 2.4/1 | 125 | 0.84 | 0.95/1 |
| 10 | FL | 31.25 | 0.729 | 2.4/1 | 125 | 5.00 | 3.56/1 |
| 11 | CIS-1,2DPCH | 31.25 | 0.729 | 2.4/1 | 125 | 1.39 | 2.03/1 |
| 12 | DIOP | 31.25 | 0.729 | 2.4/1 | 125 | 5.16 | 4.02/1 |
| 13 | 1,4-BUT | 31.25 | 0.729 | 2.4/1 | 125 | 1.25 | 2.45/1 |
| 14 | 1,3-PROP | 31.25 | 0.729 | 2.4/1 | 125 | 0.97 | 0.84/1 |
| 15 | 1,5-PENT | 31.25 | 0.729 | 2.4/1 | 125 | 2.32 | 2.28/1 |
| 16 | 1,6-HEX | 31.25 | 0.729 | 2.4/1 | 125 | 4.00 | 1.51/1 |
| 17 | O-XYL | 31.25 | 0.729 | 2.4/1 | 125 | 3.10 | 2.41/1 |
| 18 | TPP | 15.00 | 18.13 | 124/1 | 125 | 9.41 | 2.43/1 |

Above Ligand Identifications
BISBI = 2,2'-bis(diphenylphosphinomethyl)-1,1'-biphenyl
BDBMB = 2,2'-bis(dibenzylphosphinomethyl)-1,1'-biphenyl
BPBMB = 2,2'-bis(phenylbenzylphosphinomethyl)-1,1'-biphenyl
BIBMB = 2,2'-bis(diisobutylphosphinomethyl)-1,1'-biphenyl
TR-DMCB = trans-1,2-bis(diphenylphosphinomethyl)-3,3-dimethylcyclobutane
TR-DMECB = trans-trans-1,2-bis(diphenylphosphinomethyl)-3-ethoxy-4,4-dimethylcyclobutane
TR-DPNOR = trans-2,3-bis(diphenylphosphinomethyl)[2.2.1]bicycloheptane
1,8-DINAP = 1,8-bis(diphenylphosphinomethyl)naphthalene
CIS-DPNOR = endo, cis-2,3-bis(diphenylphosphinomethyl)[2.2.1]bicycloheptane
FL = 1,1'-bis(diphenylphosphino)ferrocene
CIS-1,2DPCH = cis-1,2-bis(diphenylphosphinomethyl)cyclohexane
DIOP = (-)-2,3-O—isopropylidene-2,3-dihydroxy-1,4-bis(diphenylphosphino)butane
1,4-BUT = 1,4-bis(diphenylphosphino)butane
1,3-PROP = 1,3-bis(diphenylphosphino)propane
1,5-PENT = 1,5-bis(diphenylphosphino)pentane
1,6-HEX = 1,6-bis(diphenylphosphino)hexane
O-XYL = a,a'-bis(diphenylphosphino)orthoxylene
TPP = triphenylphosphine

TABLE 2
Effect of Reaction Temperature of BISBI/Rh Catalyst

| Run No. | Rh Charge, mg | Ligand Charge, mmol | L/Rh Mole Ratio | Reactor Temp, °C. | Catalyst Activity, lb HBu/g Rh-hr | HBu N/Iso Ratio |
|---|---|---|---|---|---|---|
| 19 | 31.25 | 0.729 | 2.4/1 | 125 | 5.80 | 25.1/1 |
| 20 | 31.25 | 0.729 | 2.4/1 | 115 | 3.43 | 27.2/1 |
| 21 | 31.25 | 0.729 | 2.4/1 | 105 | 2.21 | 28.7/1 |
| 22 | 31.25 | 0.729 | 2.4/1 | 95 | 0.86 | 32.2/1 |

The invention has been described in detail with particular reference to preferred embodiments thereof, but it will be understood that variations and modifications can be effected within the spirit and scope of the invention.

We claim:

1. A compound of the formula

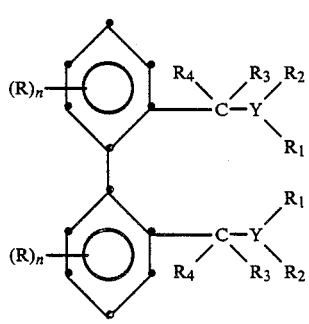

wherein
n is 1-4;
each R is independently selected from hydrogen, alkyl, alkoxy, aryloxy, aryl, aralkyl, alkaryl, alkoxyalkyl, cycloaliphatic, halogen, alkanoyl, alkanoyloxy, alkoxycarbonyl, carboxyl or cyano;
each $R_1$ and $R_2$ is independently selected from alkyl, aryl, aralkyl, alkaryl or cycloaliphatic;
each $R_3$ and $R_4$ is independently selected from hydrogen and the $R_1$ substituents;
each Y is independently selected from the elements P, As, Sb and Bi; and
each alkyl group or moiety is straight or branched chain of 1 to 20 carbons, and each cycloaliphatic group contains from 4 to 6 ring carbons.

2. The compound of claim 1 wherein R is hydrogen, $R_1$ and $R_2$ are alkyl or phenyl, and $R_3$ and $R_4$ are hydrogen or phenyl.

3. A compound in accordance with claim 1 selected from:
2,2'-bis(diphenylphosphinomethyl)-1,1'-biphenyl;
2,2'-bis(dibenzylphosphinomethyl)-1,1'-biphenyl;
2,2'-bis(phenylbenzylphosphinomethyl)-1,1'-biphenyl;
2,2'-bis(diisobutylphosphinomethyl)-1,1'-biphenyl; and mixtures thereof.

4. A compound in accordance with claim 1 wherein said compound is 2,2'-bis-(diphenylphosphinomethyl)-1,1'-biphenyl.

* * * * *